(12) United States Patent
Hancock et al.

(10) Patent No.: US 10,080,609 B2
(45) Date of Patent: Sep. 25, 2018

(54) ELECTROSURGICAL APPARATUS (71) Applicant: CREO MEDICAL LIMITED, Chepstow, Monmouthshire (GB)

(72) Inventors: Christopher Paul Hancock, Chepstow (GB); Malcolm White, Chepstow (GB); Francis Amoah, Chepstow (GB); Nuwan Dharmisiri, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 669 days.

(21) Appl. No.: 14/431,684

(22) PCT Filed: Sep. 16, 2013

(86) PCT No.: PCT/GB2013/052413
§ 371 (c)(1),
(2) Date: Mar. 26, 2015

(87) PCT Pub. No.: WO2014/049332
PCT Pub. Date: Apr. 3, 2014

(65) Prior Publication Data
US 2015/0238257 A1    Aug. 27, 2015

(30) Foreign Application Priority Data

Sep. 27, 2012 (GB) .................................. 1217247.4

(51) Int. Cl.
*A61B 18/04* (2006.01)
*A61B 18/18* (2006.01)
*A61B 18/12* (2006.01)
*H01P 1/208* (2006.01)
(Continued)

(52) U.S. Cl.
CPC .......... *A61B 18/1815* (2013.01); *A61B 18/12* (2013.01); *A61B 18/1206* (2013.01);
(Continued)

(58) Field of Classification Search
CPC .......... H01P 1/208; H01P 1/365; A61B 18/12; A61B 18/1206; A61B 18/14;
(Continued)

(56) References Cited

U.S. PATENT DOCUMENTS

| 4,091,344 A | 5/1978 | Latourrette |
| 5,088,997 A * | 2/1992 | Delahuerga .......... A61B 18/042 |
| | | 606/37 |

(Continued)

FOREIGN PATENT DOCUMENTS

| GB | 2486343 A | 6/2012 |
| JP | 2012-143568 A | 8/2012 |

OTHER PUBLICATIONS

International Search Report of PCT/GB2013/052413 dated Jan. 17, 2014.

*Primary Examiner* — Daniel Fowler
(74) *Attorney, Agent, or Firm* — Arent Fox LLP (57) ABSTRACT

An electrosurgical apparatus having a feed structure comprising a radiofrequency (RF) channel for conveying RF electromagnetic (EM) radiation from an RF signal generator to a probe and a microwave channel for conveying microwave EM radiation from a microwave signal generator to the probe, wherein the RF channel and microwave channel comprise physically separate signal pathways, wherein the feed structure includes a combining circuit having an input connected to the signal pathway on the RF channel, another input connected to the signal pathway on the microwave channel, and an output connected to a common signal pathway for conveying the RE EM radiation and EM radiation separately or simultaneously to the probe, and wherein the microwave channel includes a waveguide isolator connected to isolate the signal pathway on the microwave channel from the RF EM radiation.

21 Claims, 8 Drawing Sheets (51) Int. Cl.
  *H01P 1/365* (2006.01)
  *A61B 18/14* (2006.01)
  *A61B 18/00* (2006.01)
(52) U.S. Cl.
  CPC .............. *A61B 18/14* (2013.01); *H01P 1/208* (2013.01); *H01P 1/365* (2013.01); *A61B 2018/00166* (2013.01); *A61B 2018/00601* (2013.01); *A61B 2018/00916* (2013.01); *A61B 2018/00994* (2013.01); *A61B 2018/128* (2013.01); *A61B 2018/1293* (2013.01); *A61B 2018/1823* (2013.01); *A61B 2018/1876* (2013.01); *A61B 2018/1892* (2013.01)
(58) Field of Classification Search
  CPC ...... A61B 18/1815; A61B 2018/00166; A61B 2018/00601; A61B 2018/00916; A61B 2018/00994; A61B 2018/128; A61B 2018/1293; A61B 2018/1823; A61B 2018/1876; A61B 2018/1892
  See application file for complete search history.

(56) References Cited

U.S. PATENT DOCUMENTS

| | | | | |
|---|---|---|---|---|
| 5,372,596 | A | * | 12/1994 | Klicek .................. A61B 18/12 606/34 |
| 5,931,836 | A | * | 8/1999 | Hatta .................. A61B 18/1206 606/34 |
| 2006/0155270 | A1 | * | 7/2006 | Hancock ................ A61B 18/18 606/33 |
| 2010/0168727 | A1 | * | 7/2010 | Hancock ................ A61B 18/18 606/33 |
| 2010/0185191 | A1 | * | 7/2010 | Carr .................... A61B 5/0507 606/33 |
| 2010/0278197 | A1 | | 11/2010 | Di et al. |
| 2010/0298822 | A1 | * | 11/2010 | Behnke ................. A61B 18/18 606/33 |
| 2011/0121735 | A1 | * | 5/2011 | Penny .................. A61B 18/042 315/111.21 |
| 2011/0208179 | A1 | | 8/2011 | Prakash et al. |
| 2013/0267943 | A1 | | 10/2013 | Hancock |

\* cited by examiner

ELECTROSURGICAL APPARATUS

CROSS-REFERENCE TO RELATED APPLICATION

This application is a National Stage entry of International Application No. PCT/GB2013/052413, filed Sep. 16, 2013, which claims priority to United Kingdom Patent Application No. 1217247.4, filed Sep. 27, 2012. The disclosures of the priority applications are incorporated in their entirety herein by reference.

FIELD OF THE INVENTION

The invention relates to electrosurgical apparatus in which radiofrequency energy and microwave frequency energy are used to treat biological tissue. In particular, the invention relates to surgical apparatus capable of generating radiofrequency (RE) energy for cutting tissue and microwave frequency energy for haemostasis (i.e. sealing broken blood vessels by promoting blood coagulation).

BACKGROUND OF THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Instead of a sharp blade, it is known to use radiofrequency (RF) energy to cut biological tissue. The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, that cannot be controlled by the cell membrane, resulting in the cell rupturing. When this occurs over a wide area it can be seen that tissue has been transected.

Whilst the above principle works elegantly in lean tissue, it is less efficient in fatty tissue because there are fewer ionic constituents to aid the passage of electrons. This means that the energy required to vaporise the contents of the cells is much greater, as the latent heat of vaporisation of fat is much greater than that of water.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured and changes from a rod like molecule to a coil, which causes the vessel to contract and reduce in size, giving the clot an anchor point, and a smaller area to plug.

However, RF coagulation is less efficient when fatty tissue is present because the electrical effect is diminished. It can thus be very difficult to seal fatty bleeders. Instead of having clean white margins, the tissue has a blackened, burned appearance.

In practice, a RF device may operate using a waveform with a medium crest factor that is midway between a cutting and coagulating output.

GB 2 486 343 discloses a control system for an electrosurgical apparatus in which the energy delivery profile of both RF energy and microwave energy delivered to a probe is set based on sampled voltage and current information of RF energy conveyed to the probe and sampled forward and reflected power information for the microwave energy conveyed to and from the probe.

Figure 1:
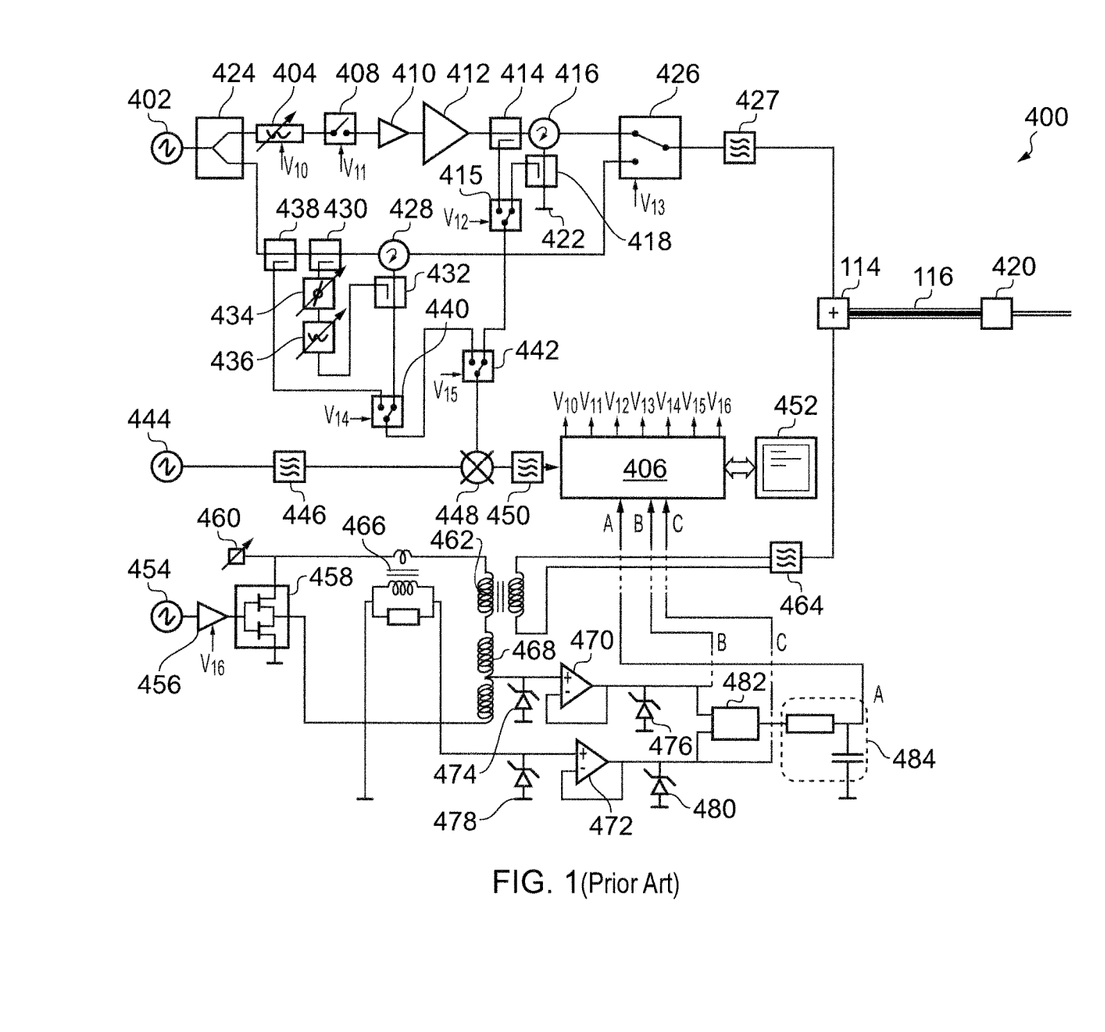
FIG. 1 is an overall schematic system diagram of electrosurgical apparatus in which the present invention may be used, and is discussed above.

FIG. 1 shows a schematic diagram of an electrosurgical apparatus 400 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

SUMMARY OF THE INVENTION

The present invention provides an enhancement to the electrosurgical apparatus disclosed GB 2 486 343. The enhancement concerns the components used to isolate the probe from the mains energy used to power the apparatus.

At its most general, the present invention proposes using a waveguide isolator at the junction between the microwave channel and signal combiner. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV).

The invention may provide a capacitive structure at or adjacent the waveguide that can reduce capacitive coupling across the isolation barrier. The reduced capacitive coupling may be provided by connecting the waveguide isolator (in particular the outer conductor of the waveguide isolator) in series with an additional capacitive component, such as a coaxial isolator. To maintain the reduced capacitive coupling during operation, the additional capacitive component may have a high breakdown voltage, e.g. 500 V or more. Thus, the waveguide isolator and additional capacitive component (e.g. coaxial isolator) may act in combination as a low frequency blocking filter to prevent RF EM radiation from the RF channel from entering the microwave channel.

Alternatively, in a preferred embodiment the capacitive structure may be an integral part of the DC isolation barrier in the waveguide isolator itself. For example, reduced capacitive coupling can be achieved by decreasing the capacitance or increasing the capacitive reactance of the isolating gap formed in the outer conductor of the waveguide isolator, e.g. by increasing the thickness of insulating material present in the gap. In this arrangement, the waveguide isolator may include a choke to minimise leakage of microwave power at the gap.

The advantage of using a waveguide isolator as described above is that it both provides a high withstand voltage and prevents unwanted capacitive coupling between the conductive parts of the waveguide isolator. Without the reduced capacitive coupling, there is a risk of a patient or user in contact with the waveguide isolator forming part of a current path resulting from the capacitive coupling, especially in the outer conductor of the waveguide isolator. Such a risk may affect the ability of the apparatus to meet the necessary electrical safety standards for medical devices (e.g. as set by International Electrotechnical Commission (IEC) standard 60601-2).

The invention effectively increases the capacitive reactance of the isolation component and hence inhibits the capacitive coupling.

According to the invention, there may be provided electrosurgical apparatus for resection of biological tissue, the apparatus comprising: a radiofrequency (RF) signal generator for generating RF electromagnetic (EM) radiation having a first frequency; a microwave signal generator for generating microwave EM radiation having a second frequency that is higher than the first frequency; a probe arranged to deliver the RF EM radiation and the microwave EM radiation separately or simultaneously from a distal end thereof; and a feed structure for conveying the RF EM radiation and the microwave EM radiation to the probe, the feed structure comprising an RF channel for connecting the probe to the RF signal generator, and a microwave channel for connecting the probe to the microwave signal generator, wherein the RF channel and microwave channel comprise physically separate signal pathways from the RF signal generator and microwave signal generator respectively, wherein the feed structure includes a combining circuit having a first input connected to the separate signal pathway on the RF channel, a second input connected to the separate signal pathway on the microwave channel, and an output connected to a common signal pathway for conveying the RF EM radiation and the microwave EM radiation separately or simultaneously along a single channel to the probe, and wherein the microwave channel includes a waveguide isolator connected to isolate the separate signal pathway on the microwave channel from the RF EM radiation.

The waveguide isolator may comprise a conductive input section, a conductive output section which mates with the input section to define a waveguide cavity within a volume enclosed by the input and output sections, and a DC isolation barrier arranged between the input and output sections. The waveguide cavity may be cylindrical. The output on the common signal pathway may include a signal conductor and a ground conductor, and the feed structure may include a capacitive structure between the ground conductor of the output on the common signal pathway and the conductive input section of the waveguide isolator, the capacitive structure being arranged to inhibit coupling of the RF EM energy and leakage of the microwave EM energy.

As mentioned above, in a preferred embodiment the capacitive structure may be provided by the DC isolation barrier and a microwave choke formed on the input section of the waveguide isolator. Where the inner and outer sections of the waveguide isolator define a cylindrical body, the microwave choke may comprise an annular channel extending axially from the distal end of the inner section of the waveguide isolator. The channel may be filled with air or another suitable dielectric. The axial length of the choke may be a quarter wavelength of the microwave EM energy (or an odd multiple thereof) in the material (e.g. air) and geometrical structure of the channel.

The DC isolation barrier itself may include a rigid insulating spacer element mounted between the inner and outer sections of the waveguide isolator. The spacer element may be formed from an insulating plastic, such as Delrin®. In the waveguide is cylindrical, the spacer element may comprise an annular sleeve mounted over the distal end of one of the input or output sections of the waveguide isolator. The outer surface of the sleeve may be flush with the outer surface of the input and output sections.

The axial length of the overlap between the sleeve and the inner and/or outer sections is preferably an odd number of quarter wavelengths (usually one quarter wavelength) at the microwave frequency in the material of the sleeve and the structure containing it. The thickness of the insulating layer (radial thickness when it is an insulating sleeve) may be selected to be either as thin as possible to minimise microwave leakage or as thick as necessary to reduce the capacitance to a level that provides the required isolation at the frequency of the RF EM energy. These two requirements are in conflict and it may be that they cannot both be met. In practice, the sleeve may thus comprise either (i) a thin insulating layer, which meets the microwave leakage requirement but requires an additional capacitive break in series with the outer conductor in order to reduce the capacitance (e.g. the coaxial isolator discussed below), or (ii) a thick insulating layer, which meets the RF REM energy isolation requirement, but requires an additional microwave component to achieve the required low microwave leakage (e.g. the microwave choke discussed above).

The DC isolation barrier may includes additional components. For example, the DC isolation barrier may include an insulating film mounted on a portion of the inner surface of the input section at the junction with the rigid insulating spacer element. The insulating film may extend away from the rigid insulating spacer element by a predetermined distance, e.g. to increase the surface breakdown voltage.

The waveguide isolator allows the combining circuit to float electrically, which increases safety. The capacitive structure acts to increase the capacitive reactance of the combining circuit to reduce the risk of an RF signal escaping down the microwave channel via a capacitive coupling through the waveguide isolator.

In another embodiment, the capacitive structure may comprise an additional capacitance connected in series with the waveguide isolator. The additional capacitance may be a coaxial isolator. The additional capacitance may need to have a high breakdown voltage to cope with the peak voltages seen within the system. The breakdown voltage of the additional capacitance may be 1 kV or more, preferably 2 kV or more.

Using the adapted waveguide isolator mentioned above or the series-connected waveguide isolator and coaxial isolator as a high pass filter may overcome three disadvantages of using a single high frequency capacitor to provide the necessary isolation. Firstly, it is desirable for the entire combining circuit to be floating, i.e. without a direct path to ground or the mains power. Thus, both the signal and ground planes from the microwave channel need to enter the combining circuit capacitively. The waveguide isolator can provide this property. Secondly, it is desirable to prevent the RF signal from leaking out to the patient or user through capacitive coupling across the waveguide isolator. The adapted DC isolation barrier described above or the coaxial isolator can provide the necessary capacitance to increase the capacitive reactance of the junction and hence inhibit the capacitive coupling at the first frequency. A coaxial isolator is preferred to a normal capacitor because the RF signal may be supplied as high voltage pulses (e.g. of 5 kV or higher), which is higher than the typical voltage breakdown of a normal capacitor. Thirdly, the insertion loss of the series arrangement is much lower than for a normal capacitor at the preferred microwave frequencies disclosed herein (e.g. 5.8 GHz or higher), which can help to prevent the circuit resonating a certain frequencies.

The invention may be combined with any or all of the components (either individually or in any combination) described above with reference to the electrosurgical apparatus 400 as set out in GB 2 486 343. For example, the RF channel and microwave channel may include any or all of the components of the RF channel and microwave channel respectively described above.

The separate signal pathway on the RF channel may be isolated from the microwave EM radiation. The RF channel may therefore include an isolator, e.g. a low pass, band pass, band stop or notch filter, connected between the separate signal pathway on the RF channel and the combining circuit. The low pass, band pass, band stop or notch filter may be integrated with the combining circuit. For example, in one embodiment, the combining circuit may comprise a T-shaped open microstrip bi-direction diplexer circuit having a low pass, band pass, band stop or notch filter integrally formed therewith to prevent microwave EM radiation from leaking out of the first input. The band stop filter may comprise a plurality of stubs (e.g. two, three or four stubs) formed on the microstrip line between the first input and T-junction of the diplexer circuit.

However, in a preferred embodiment the combining circuit is integrated with the waveguide isolator. The separate signal pathway on the RF channel may terminate at an RF connector which is connected into the waveguide isolator, whereby the RF signal is directly conveyed to an output port of the waveguide isolator. The common signal pathway may thus extend away from the output port of the waveguide isolator. Thus, the output connected to common signal pathway may include an output probe mounted on the output section of the waveguide isolator, the output probe having a coupling conductor extending into the waveguide isolator to couple the microwave EM energy therefrom. The first input may include an RF connector mounted on the waveguide isolator, the RF connector having a signal conductor that extends into the waveguide cavity to electrically contact the coupling conductor of the output probe. The signal conductor may be an insulated conductive wire or rod. The signal conductor may contact the coupling conductor at a predetermined distance from its tip. The distance may be adjustable, e.g. by changing the position of the RF connected with respect to the waveguide isolator. Preferably the position of the signal conductor is aligned close to an equipotential of the microwave EM energy within the microwave isolator, so the presence of the RF connector does not affect the behaviour of the microwave EM energy.

Integrating the combining circuit with the adapted waveguide isolator provides a single component which provides the necessary generator-to-patient isolation whilst avoiding unwanted RF coupling and microwave leakage. In addition this single component obviates the need for a separate multi-stub (low pass) rejection filter on the RF channel. Moreover, the integrated nature of the component means that the insertion loss of the device is much lower (there is no microstrip board, fewer interconnections, fewer microwave routing cables, no co-axial isolator). The integrated waveguide isolator is also physically smaller and easier to manufacture than the multi-component solution.

The apparatus may include a controller operable to select an energy delivery profile for the RF EM radiation and the microwave EM radiation. Herein, energy delivery profile may mean the shape of the waveform in terms of voltage/current and time for the RF energy and power level and time for the microwave energy. Control of the energy delivery profile can permit a range of therapeutic applications to be realised.

The apparatus may include an RF signal detector for sampling current and voltage on the RF channel and generating therefrom a RF detection signal indicative of the phase difference between the current and voltage. The controller may be in communication with the RF signal detector to receive the RF detection signal and select the energy delivery profile for the RF EM radiation based on the RF detection signal.

Similarly, the apparatus may include a microwave signal detector for sampling forward and reflected power on the microwave channel and generating therefrom a microwave detection signal indicative of the magnitude and/or phase of microwave power delivered by the probe. The controller may be in communication with the microwave signal detector to receive the microwave detection signal and select the energy delivery profile for the microwave EM radiation based on the microwave detection signal.

Thus, the system may be configured to provide secure control over the output of the electrosurgical apparatus. For example, the apparatus may enable selection of an energy delivery profile for tissue cutting which may comprise delivering continuous wave (CW) RF EM energy with a 400 V peak amplitude at a power level of 30 W. The controller may be adjustable (e.g. manually adjustable) to vary the peak amplitude and power level. Because the RF and microwave EM radiation are monitored, the energy delivered to the tissue can be determined with accuracy. In another example, the apparatus may enable selection of an energy delivery profile for coagulation may comprise delivering continuous wave (CW) microwave EM energy at a power level of 25 W. Again, the controller may be adjustable (e.g. manually adjustable) to vary the power level.

More generally, to achieve tissue cutting in a dry environment, it may be necessary to deliver a 500 kHz continuous wave sinusoidal waveform with a peak voltage of amplitude 400 V and a power setting of 40 W, whereas to achieve tissue cutting in a wet environment, it may be necessary to deliver one or more bursts of 500 kHz energy with a peak voltage of 4000 V with a peak power of 200 W and a duty cycle of 10%, which may be set up in the form whereby the ON time is 10 ms and the OFF time is 90 ms. This kind of pulsed energy delivery profile may ensure that the energy is passed to the tissue rather than causing undesirable heating of the surrounding fluid. For efficient tissue coagulation in dry tissue, CW microwave power may be delivered into tissue at an RMS power level of 30 W. For coagulation in a wet environment, the microwave power may be pulsed, e.g. having a peak power of 100 W with a 30% duty cycle.

Other waveforms that produce desirable therapeutic tissue affects may include a combination of RF and microwave energy delivered in CW and pulsed formats similar to those described above. The RF and microwave energy may be delivered simultaneously where the microwave energy modulates the RF energy. For example, a 400 V peak 500 kHz CW RF profile may be modulated with a 10 W CW 5.8 GHz microwave signal to produce a degree of tissue coagulation during the resection process to reduce bleeding when an organ or a section of an organ is being removed.

All waveform parameters may be adjustable by the controller, e.g. via a user interface.

The control system may comprise a dedicated measurement channel, for delivering energy (preferably microwave energy) at a low power level (e.g. 10 mW or less). The system may thus make available measurement signals from a channel that is not delivering therapeutic effects, i.e. the waveform or energy delivery into tissue may be controlled based on low power measurements made using a channel that is not involved in delivering therapeutic tissue effects. The measurement channel may be use the same source as the microwave channel. The system may be switchable so that microwave energy is delivered either through the measurement channel (in a "measurement mode") or through the microwave channel (in a "treatment mode"). Alternatively, the microwave channel may be switchable between a low power mode (for measurement) and a high power mode (for treatment). In this arrangement a separate measurement channel is not needed.

The system may be configured to supply energy for cutting and coagulating tissue simultaneously (e.g. a mixed or blend mode) or may be operated independently, whereby the RF and microwave energy is delivered to the probe under manual user control (e.g. based on the operation of a footswitch pedal) or automatically based on measured phase and/or magnitude information from the RF and/or microwave channel. The system may be used to perform tissue ablation and cutting. In the instance where microwave and RF energy are delivered simultaneously, either or both RF and microwave energy returned to the respective generators may be used at high power or low power to control the energy delivery profile. In this instance, it may be desirable to take measurements during the OFF time when the energy delivery format is pulsed.

The distal end of the probe may comprise a bipolar emitting structure comprising a first conductor spatially separated from a second conductor, the first and second conductors being arranged to act: as active and return electrodes respectively to convey the RF EM radiation by conduction, and as an antenna or transformer to facilitate radiation of the microwave EM energy. Thus, the system may be arranged to provide a local return path for RF energy. For example, the RF energy may pass by conduction through the tissue separating the conductors, or a plasma may be generated in the vicinity of the conductors to provide the local return path. RF tissue cutting may be produced by a fixed dielectric material separating the first and second conductors, where the thickness of the dielectric material is small, i.e. less than 1 mm and the dielectric constant high, i.e. greater than that of air.

The invention may be particularly suitable in gastrointestinal (GI) procedures, e.g. to remove polyps on the bowel, i.e. for endoscopic sub-mucosal resection. The invention may also lend itself to precision endoscopic procedures, i.e. precision endoscopic resection, and may be used in ear, nose and throat procedures and liver resection.

The first frequency may be a stable fixed frequency in the range 10 kHz to 300 MHz and the second frequency may be a stable fixed frequency in the range 300 MHz to 100 GHz. The first frequency should be high enough to prevent the energy from causing nerve stimulation and low enough to prevent the energy from causing tissue blanching or unnecessary thermal margin or damage to the tissue structure. Preferred spot frequencies for the first frequency include any one or more of: 100 kHz, 250 kHz, 500 kHz, 1 MHz, 5 MHz. Preferred spot frequencies for the second frequency include 915 MHz, 2.45 GHz, 5.8 GHz, 14.5 GHz, 24 GHz. Preferably the second frequency is at least an order of magnitude (i.e. at least 10 times) higher than the first frequency.

In another aspect, the invention may be expressed as an isolating circuit for electrosurgical apparatus for resection of biological tissue, the isolating circuit comprising: a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and a waveguide isolator connected to isolate the microwave channel from the RF EM radiation, wherein the waveguide isolator comprises a conductive input section, a conductive output section which mates with the input section to define a waveguide cavity within a volume enclosed by the input and output sections, and a DC isolation barrier arranged between the input and output sections, wherein the output from the combining circuit includes a signal conductor and a ground conductor, and wherein the isolating circuit comprises a capacitive structure between the ground conductor of the output from the combining circuit and the conductive input section of the waveguide isolator, the capacitive structure being arranged to inhibit coupling of the RF EM energy and leakage of the microwave EM energy. Features of the combining circuit, waveguide isolator and capacitive structure described above may also be applicable to this aspect of the invention.

BRIEF DESCRIPTION OF THE DRAWINGS

Examples of the present invention are discussed in detail below with reference to the accompanying drawings, in which.

DETAILED DESCRIPTION; FURTHER OPTIONS AND PREFERENCES

Figure 2:
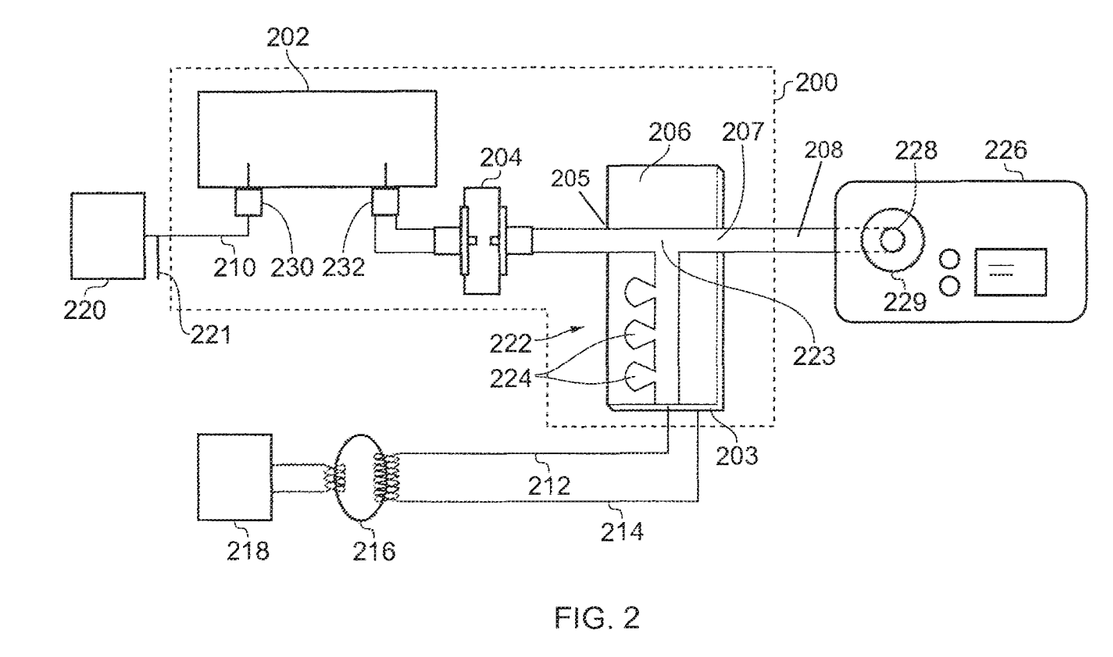
FIG. 2 is a schematic diagram of an isolating circuit in an electrosurgical apparatus that is an embodiment of the invention.

FIG. 2 is a schematic diagram of an isolating circuit 200 for an electrosurgical apparatus that is an embodiment of the invention. The isolating circuit 200 forms part of a feed structure for conveying RF EM radiation from an RF signal generator 218 and microwave radiation from a microwave signal generator 220 to a probe. In this embodiment, the probe (not shown) is connectable to an output port 228 provided in a housing 226. The feed structure comprises an RF channel having a RF signal pathway 212, 214 for conveying the RF EM radiation and a microwave channel having a microwave signal pathway 210 for conveying the microwave EM radiation. The signal pathways for the RF EM radiation and microwave radiation are physically separate from each other. The RF signal generator is connected to the RF signal pathway 212, 214 via a voltage transformer 216. The secondary coil of the transformer 216 (i.e. on the probe side of the arrangement) is floating, so there is not a direct current path between the patient and the RF signal generator 218. This means that both the signal conductor 212 and ground conductor 214 of the RF signal pathway 212, 214 are floating.

A combining circuit 206 has a first input 203 for connecting to the RF signal pathway 212, 214, and a second input 205 for connecting to the microwave signal pathway 210. The combining circuit 206 joins the pathways to an output 207, which is connected to a common signal pathway 208. The common signal pathway 208, which may include a flexible cable (e.g. coaxial cable of the like) conveys the RF EM radiation and microwave EM radiation to the probe. In this embodiment the combining circuit 206 comprises a T-shaped microstrip junction formed on a low loss microwave dielectric substrate (e.g. a suitable type of RT/Duroid® substrate manufactured by Rogers Corporation). The ground plane of the microstrip junction, which is formed on the opposite side of the substrate from the T-shaped microstrip junction, is connected to the ground conductor 214 of the RF signal pathway 212, 214. It is therefore floating. The T-shaped microstrip junction provides the first input 203, which is connected to the signal conductor 212 of the RF signal pathway.

A band stop filter 222 is provided on the T-shaped microstrip junction in the form of three stubs 224 in shunt on the microstrip line between the first input 203 and junction 223 with the microwave microstrip line. The stub nearest the junction is spaced from it by an odd multiple of a quarter wavelength of the microwave EM radiation transmitted by the microstrip. The subsequent stubs are separated from one another by half the wavelength. Using more than one stub increase the effectiveness of the filter in preventing microwave EM radiation from escaping into the RF pathway 212, 214.

The isolating circuit 200 comprises a waveguide isolator 202 and a coaxial isolator 204 connected in series on the microwave signal pathway 210 between the microwave signal generator 220 and second input 205. The waveguide isolator 202 and coaxial isolator 204 are effectively capacitors acting as high pass filters. They permit microwave EM radiation from the microwave signal generator 220 to pass to the combining circuit 206, but prevent RF EM radiation from escaping back out of the second input 205 of the combining circuit 206 into the microwave signal generator 220.

In this embodiment, the microwave channel also include a grounded stub 221 having a length equal to an odd multiple of a quarter wavelength of the microwave EM radiation transmitted by the microstrip to short out any residual RF EM radiation that does escape through the waveguide isolator and coaxial isolator, whilst keeping the microwave transmission losses to a minimum.

The waveguide isolator 202 includes an input port 230 arranged to couple microwave EM radiation from the microwave signal generator 220 into the waveguide cavity of the waveguide isolator 202, and an output port 232 arranged to couple microwave EM radiation from the waveguide cavity to the coaxial isolator 204. The waveguide isolator 202 thus causes both the signal and ground conductors of the microwave signal pathway 210 directed into the coaxial isolator 204 (and hence into the combining circuit 206) to be floating.

An insulating sleeve 229 is provided at the output port 228 of the housing to prevent a current path for connecting the grounded casing of the housing with the floating components connected to the output port 228. The output port 228 may comprises a Type N screw thread or a quick release connector, e.g. to allow different probes to be attached to the housing.

The waveguide isolator 202 is capable of transferring the microwave EM radiation into the combining circuit 206 and on to the probe with low losses while providing sufficient levels of patient protection. An example of the waveguide isolator 202 itself is shown FIGS. 5 and 6. It consists of a cylindrical waveguide arrangement formed by telescoping together a first section 240 with a cooperating second section 242. Each section has a connector 248 for coupling microwave EM radiation into or out of the waveguide. For example, each connecter 248 may comprise a Type N receptacle plug from which an E-field probe extends into the waveguide cavity to couple microwave energy to or from the cavity.

Figure 5:
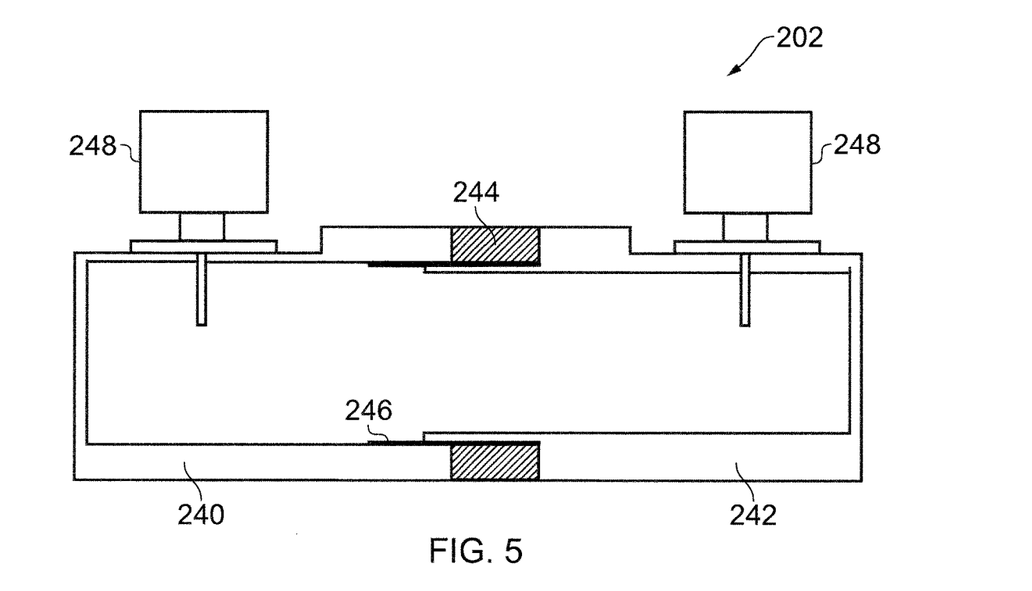
FIG. 5 is a cross-sectional side view of a waveguide isolator suitable for use in the invention.
Figure 6:
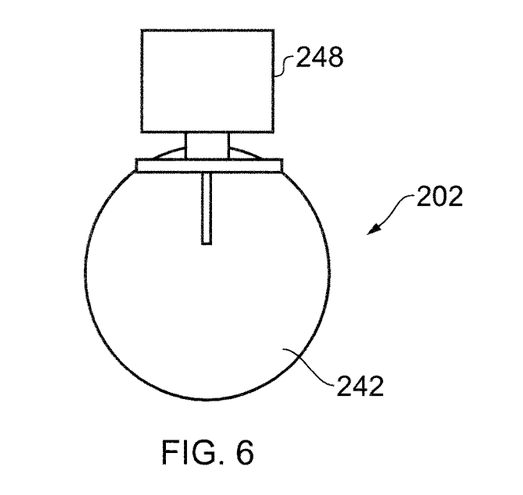
FIG. 6 is an end view of the waveguide isolator shown in FIG. 5.

The inner surfaces of the sections are separated from each other by a layer of dielectric material 246 (in this embodiment an insulation film, e.g. made of Kapton). The outer surfaces are separated by rigid insulating ring 244, e.g. made of Delrin® plastic. The waveguide isolator 202 thus provides a series capacitor on both the signal transmission path (i.e. between inner conductors) and between the ground (i.e. outer) conductors.

A cylindrical waveguide is preferred in order to meet the stringent requirements for the creepage distance and air clearances set by the International Electrotechnical Commission (IEC) standard 60601-1. In the present invention, the power and voltage levels may require the creepage distance to be at least 21 mm and the air clearance to be at least 12 mm. Other aspects of the geometry of the waveguide are determined as follows.

The distance between the end walls (which are grounded) and the centre of the E-field probe is preferably a quarter wavelength at the frequency of the microwave radiation, i.e. to transform a short circuit condition (no E-field) to an open circuit (maximum E-field). The distance between the centres of the two E-field probes is preferably a multiple of a half a wavelength at the frequency of the microwave radiation, whereby the impedances will be identical.

The dominant mode of signal propagation (which exhibits the lowest insertion loss) through a cylindrical waveguide is the $TE_{11}$ mode. The diameter D of the waveguide required to enable the signal to propagate is given by $$D = \frac{1.8412c}{\pi f \sqrt{\mu_r \epsilon_r}}$$

where c is the speed of light in a vacuum, f is the frequency of operation, $\mu_r$ is the relative permeability for a magnetic loading material (magnetic loading factor), $\epsilon_r$ is the relative permittivity for an electric loading material (dielectric loading factor), and the factor 1.8412 comes from the solution of the Bessel function for a cylindrical waveguide that supports the dominant $TE_{11}$ mode of propagation and the calculation for the cut-off frequency for lowest insertion loss at the frequency of operation.

For example, if the structure is not loaded (as is preferred to achieve the lowest insertion loss), the diameter D for the dominant mode to propagate at 5.8 GHz is greater than 30.3 mm. The actual diameter used may be chosen to take into account or exclude modes that may propagate at larger diameters. In one embodiment, the diameter is 40.3 mm.

A cylindrical waveguide is ideal for achieving the higher levels of protection noted above. However, care is needed to ensure that there is not too much capacitance across the isolated grounds (outer conductors), which may increase the amount of RF energy coupled between the RF signal path and the isolated ground, thus increasing the chances of electric shock and burns to the patient. This is illustrated in the comparative isolator circuit arrangement illustrated in FIG. 3.

Figure 3:
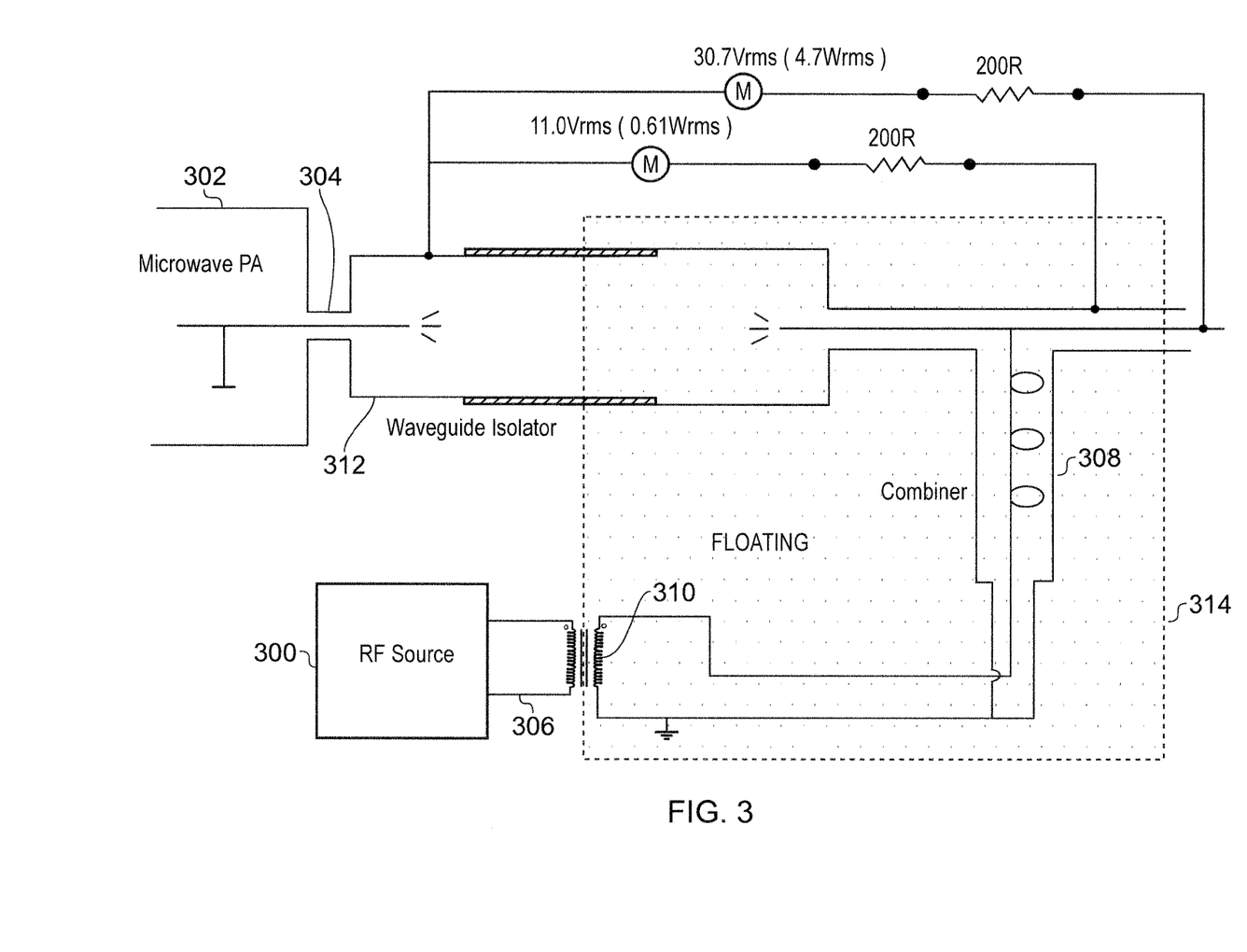
FIG. 3 is a schematic diagram of an isolating circuit having only a waveguide isolator, for comparison with the present invention.

In FIG. 3, an RF source 300 and an microwave source 302 (e.g. power amplifier) are connected to deliver RF energy and microwave energy respectively to a feed structure. Similarly to FIG. 2, the feed structure comprises an RF channel 306 for the RF energy and a microwave channel 304 for the microwave energy. The RF channel 306 and microwave channel 304 comprises physically separate pathways from their respective sources. The pathways are joined at a combining circuit 308. The RF channel 306 includes a voltage transformer 310, which isolates the combining circuit 308 from the RF source 300. The microwave channel 304 includes a waveguide isolator 312, which isolates the combining circuit 308 from the microwave source 302. Thus, both inner and outer conductors on the RF channel 306 and the microwave channel 304 on the combining circuit side of the transformer 310 and waveguide isolator respectively are floating, as indicated in FIG. 3 by dotted box 314.

The electrosurgical apparatus of the present invention is preferably capable of generating an RF signal having a power of 150 W or more. According to IEC 60601, a 150 W RF power generator may allow 1% (i.e. 1.5 Wrms) of the maximum delivered power in a 200Ω resistor least favourably connected between RF output and ground. In the comparative example shown in FIG. 3, 200Ω resistors were connected between the isolated grounds (output side and generator side) and between the isolated RF output (output side) and isolated ground (generator side). The power dissipated in these resistors was measured using an oscilloscope. The power dissipated in the 200Ω resistor connected between the RF output and isolated ground (generator side) was 4.7 Wrms, which is greater the prescribed IEC 60601 minimum.

Figure 7:
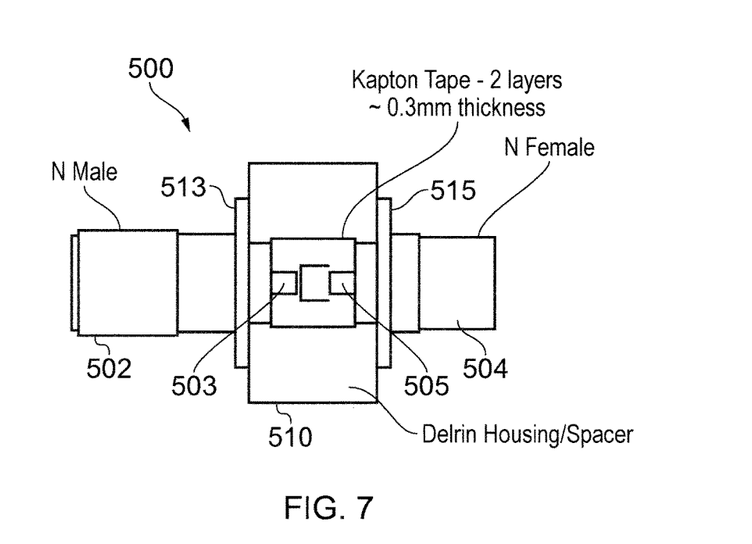
FIG. 7 is a cross-sectional side view of a coaxial isolator suitable for use in the invention.
Figure 8:
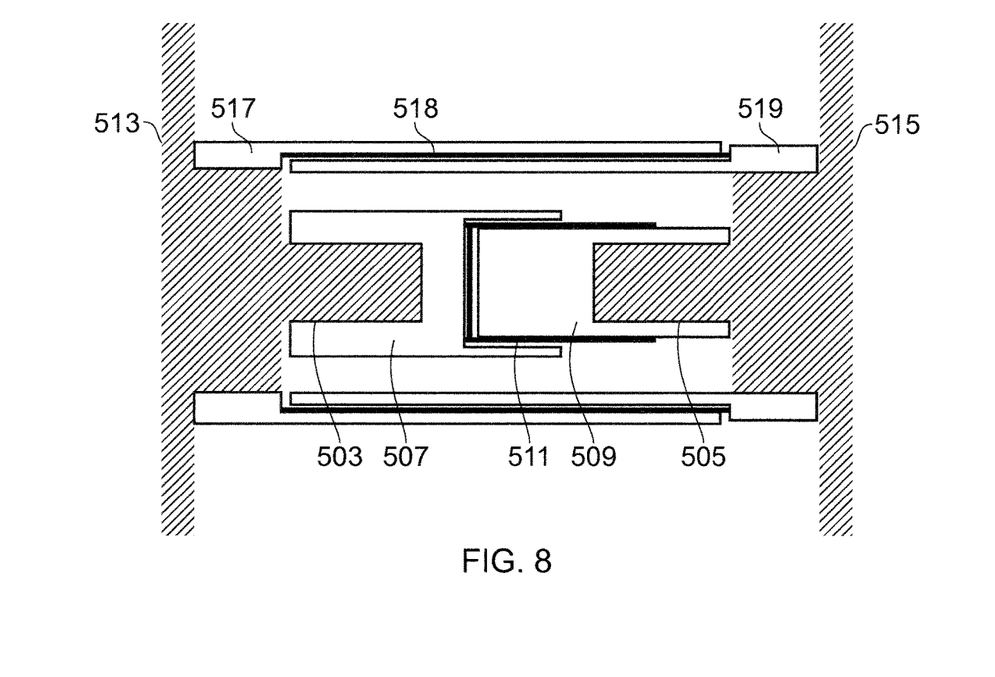
FIG. 8 is a cross-sectional side view of the components in the coaxial isolator shown in FIG. 7.

In one embodiment, the present invention provides a coaxial isolator connected in line with the waveguide isolator, i.e. in series between the waveguide isolator and the combining circuit. The coaxial isolator consists of a length of coaxial line with a series capacitor in the outer conductor. Any example of a suitable coaxial isolator 500 is shown in FIGS. 7 and 8. The coaxial isolator 500 comprises an input coaxial connector 502, which may be a Type N male connector, and an output coaxial connector 504, which may be a Type N female connector arranged opposite one another with a space therebetween.

As shown in more detail in FIG. 8, the inner conductor 503 of the input connector 502 and the inner conductor 505 of the output connector 504 each have a conductive sleeve 507, 509 mounted on their free ends. The conductive sleeve 507 of the input connector 502 defines a first cooperating part (here a recess). The conductive sleeve 509 of the output connector 504 defines a second cooperating part (here a projection) which mates with the first cooperating part. The first and second cooperating parts are separated from each other by an insulating layer 511 (e.g. of Kapton tape). The insulating layer may have a thickness of 0.3 mm or more.

Similarly, the outer conductor 513 of the input connector 502 and the outer conductor 515 of the output connector 504 each have a conductive sleeve 517, 519 mounted on their free ends. The conductive sleeves 517, 519 mate with one another. The conductive sleeves 517, 519 are separated from one another by a insulating layer 518 (e.g. of Kapton tape), and a rigid insulating spacer element 510 (e.g. of Delrin®).

Figure 4:
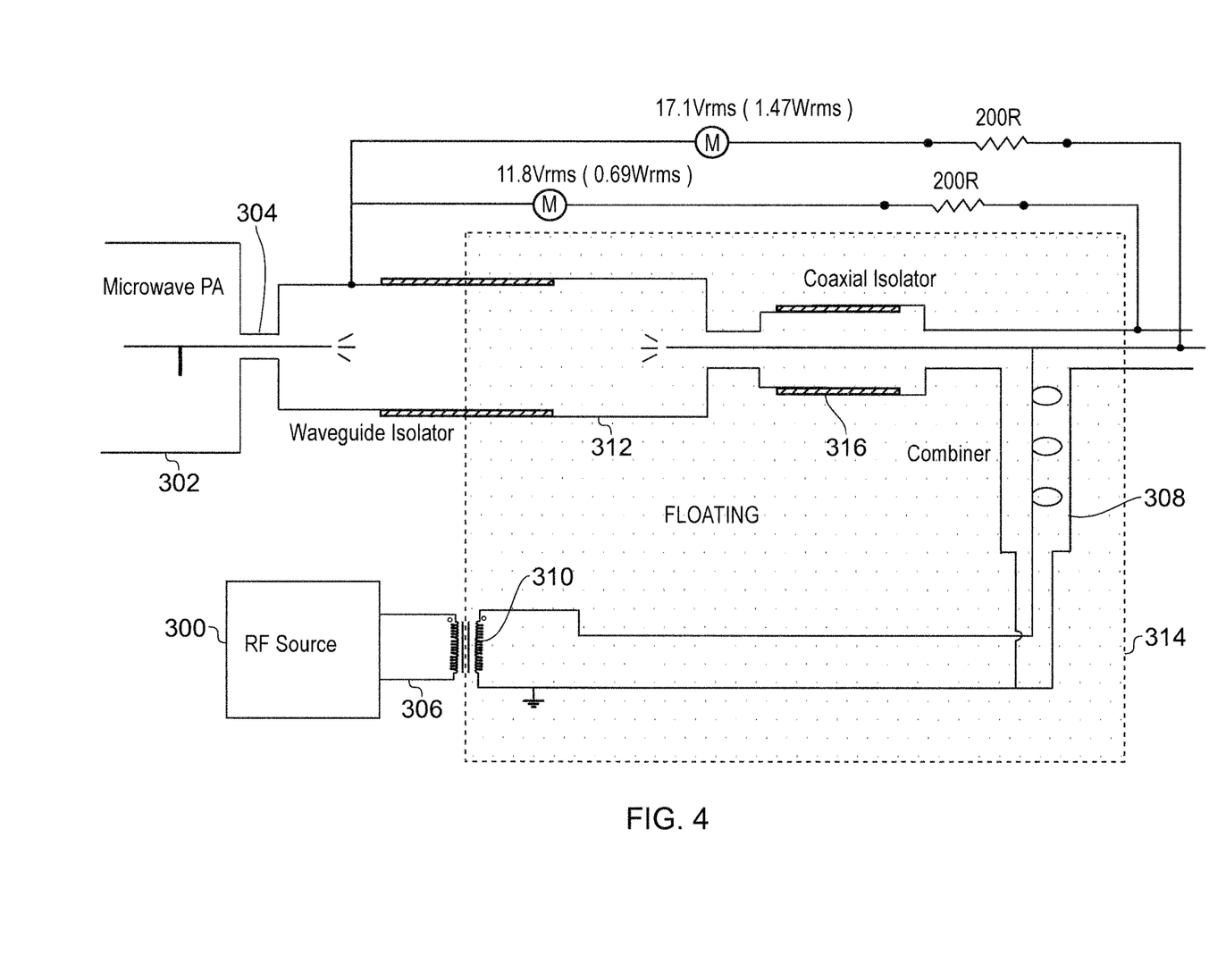
FIG. 4 is a schematic diagram of an isolating circuit according to the present invention, for comparison with FIG. 3.

The effect of the coaxial isolator is illustrated in FIG. 4, which shows an isolating circuit that is an embodiment of the invention having a coaxial isolator 316 connected between the waveguide isolator 312 and the combining circuit 308. The other components of the circuit correspond to those in FIG. 3 and are given the same reference numbers. For this arrangement, the power dissipated in a 200Ω resistor connected across the RF output and isolated ground (generator side) is 1.47 Wrms, which meets the requirements of IEC 60601.

The coaxial isolator thus provides for improved patient protection when the RF source is energised. Integrating the waveguide isolator and coaxial isolator in a single arrangement can assist in minimising microwave transmission losses.

Figure 9:
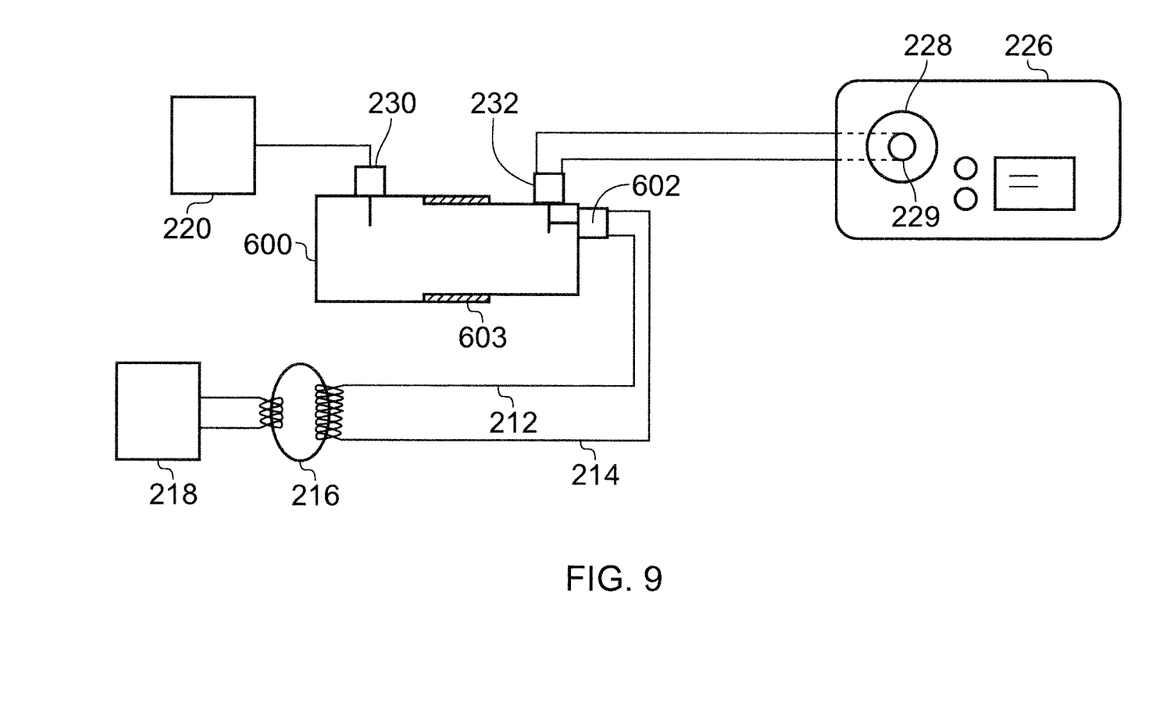
FIG. 9 is a schematic diagram of an isolating circuit in an electrosurgical apparatus that is another embodiment of the invention.

FIG. 9 is a schematic diagram showing another embodiment of an isolating circuit for an electrosurgical apparatus. Features in common with the embodiment of FIG. 2 are given the same reference numbers and are not described again. In this embodiment, the isolating circuit comprises a waveguide isolator 600 whose insulating gap is configured to provide the necessary level of DC isolation whilst also having an capacitive reactance that is high enough at the frequency of the RF energy to prevent coupling of RF energy across the insulating gap and low enough at the frequency of the microwave energy to prevent leakage of the microwave energy at the gap. The configuration of the gap is explained in detail with reference to FIG. 10. This configuration means that the coaxial isolator used in the embodiment of FIG. 2 is not needed.

In addition, in this embodiment the combining circuit is integrated with the waveguide isolator 600. The signal conductor 212 and ground conductor 214 carrying the RF signal are connected to a coaxial RF connector 602, which introduces the RF signal into the waveguide isolator 600, from where it is conveyed out from the output port 232 towards the probe. The isolating gap 603 is arranged to prevent the RF signal from coupling back into the input port 230. Microwave energy is prevented from coupling into the RF connector 602 by careful placement of the inner conductive rod within the waveguide isolator, as explained below. Combining the RF and microwave energy in the waveguide isolator obviates the need of a separate combining circuit, which reduces the number of components required for the isolating circuit and enables it to be provided as a more compact unit.

Figure 10:
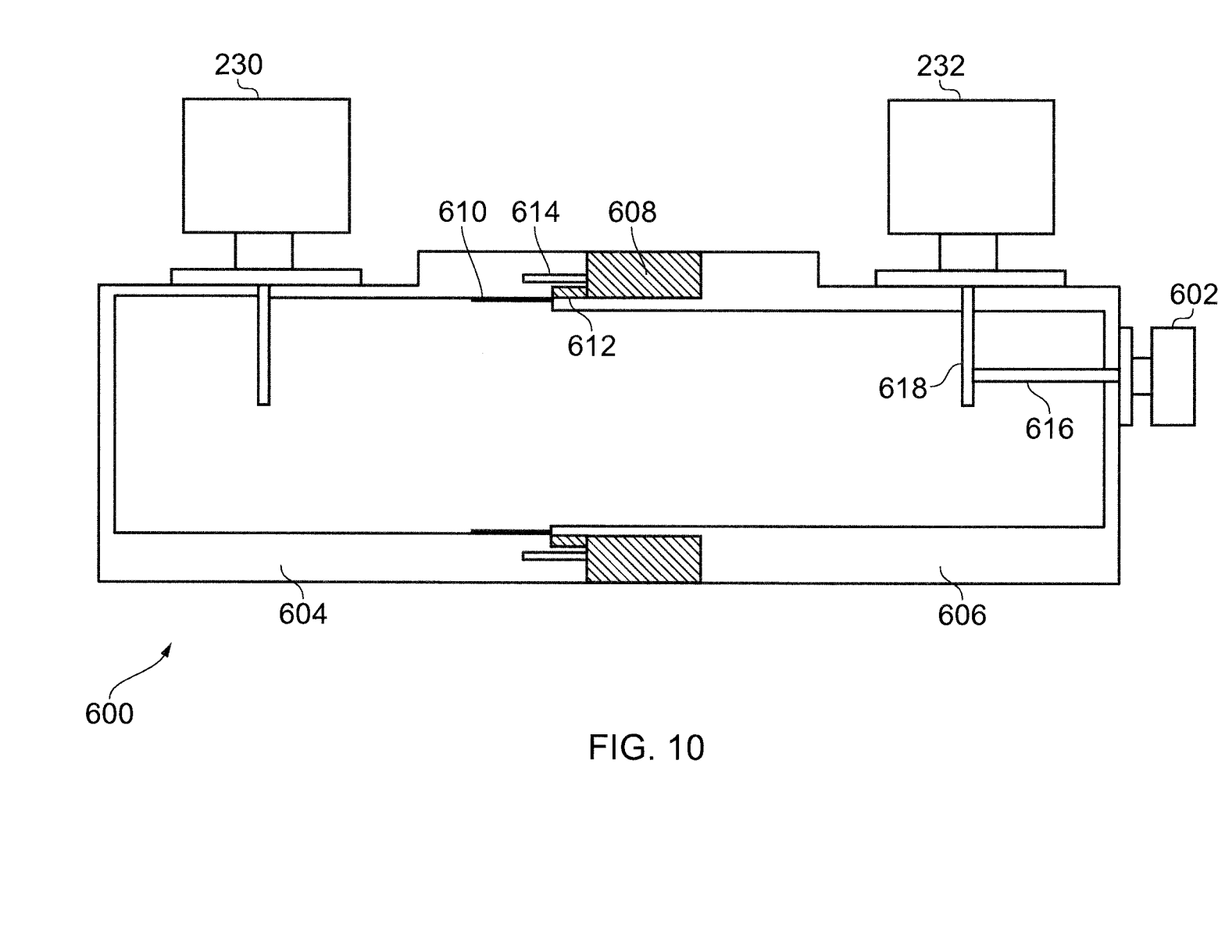
FIG. 10 is a cross-sectional side view of an adapted waveguide isolator used in the isolating circuit of FIG. 9.

FIG. 10 shows a cross-sectional side view of the adapted waveguide isolator 600 used in the isolating circuit of FIG. 9. Similarly to FIG. 5, the waveguide isolator 600 has a cylindrical body made up of two mating parts. In this embodiment, an input section 604 is a female component having an opening for receiving an output section 606, which has a cooperating male component. An input port 230 and an output port 232 are mounted on the input section 604 and output section 606 respectively in the same way as FIG. 5.

The DC gap, which insulates the input section 604 from the output section 606 comprises a number of component parts. The component parts all have rotational symmetry around the axis of the cylindrical body. A first component part is a primary insulating ring 608, e.g. made of rigid material such as Delrin® plastic, which surrounds the male component of the output section 606 and separates (and electrically isolates) the outer surfaces of the input section 604 and output section 606.

The axial length of the insulating ring 608 is shorter than the male component of the output section 606, so that a length of the male component extends beyond the distal end of the insulating ring 608. This section of the male component overlaps with the distal end of the female component of the input section 604. A second component part of the DC gap is a secondary insulating ring 612 (which may be formed in one piece with the primary insulating ring 608) which provide a radial insulation between the distal ends of the male and female components.

A third component part of the DC gap is an insulating film 610 (e.g. one or more layers of Kapton® tape) which cover the inside surface of the input section 604 for an axial length beyond the distal end of the output section 606. The insulating film can isolate the input section from any fringing fields at the distal end of the output section 606.

A fourth component part of the DC gap is an air-filled microwave choke 614, which is a narrow annular channel in the distal end of the input section 604. The presence of the microwave choke 614 lowers the capacitive reactance at the frequency of the microwave energy, which prevents leakage (e.g. radiation) of the microwave energy at the DC gap.

The increased complexity of the DC gap configuration in this embodiment increases the capacitive reactance at the frequency of the RF energy by widening the 'average' gap between the input and output sections. Meanwhile the presence of the microwave choke 614 makes use of resonant effects to ensure that the capacitive reactance at the frequency of the microwave energy is low enough to avoidance leakage of microwave energy from the gap.

In this embodiment, the waveguide isolator also acts as the combining circuit. The RF connector 602 has an inner conductive rod 616 that projects into the waveguide isolator, where it meets the inner conductor 618 of the coaxial output probe (output port 232) at a point spaced from the end of the inner conductor 618. Moreover, the position of the inner conductive rod is selected to lie substantially parallel to the equipotentials of the microwave energy in the waveguide isolator so that it does not couple any significant microwave power. This position can be determined by known simulation techniques, and may be finely tuned permitting adjustment of the radial position of the insertion point, or with a suitable tuning screw.

The invention claimed is:

1. Electrosurgical apparatus for resection of biological tissue, the apparatus comprising:
    a radiofrequency (RF) signal generator for generating RF electromagnetic (EM) radiation having a first frequency;
    a microwave signal generator for generating microwave EM radiation having a second frequency that is higher than the first frequency;
    a probe arranged to deliver the RF EM radiation and the microwave EM radiation separately or simultaneously from a distal end thereof; and
    a feed structure for conveying the RF EM radiation and the microwave EM radiation to the probe, the feed structure comprising an RF channel for connecting the probe to the RF signal generator, and a microwave channel for connecting the probe to the microwave signal generator,
    wherein the RF channel and microwave channel comprise physically separate signal pathways from the RF signal generator and microwave signal generator respectively,
    wherein the feed structure includes a combining circuit having a first input connected to the separate signal pathway on the RF channel, a second input connected to the separate signal pathway on the microwave channel, and an output connected to a common signal pathway for conveying the RF EM radiation and the microwave EM radiation separately or simultaneously along a single channel to the probe,
    wherein the microwave channel includes a waveguide isolator connected to isolate the separate signal pathway on the microwave channel from the RF EM radiation,
    wherein the combining circuit is integrated with the wavelength isolator,
    wherein the output connected to the common signal pathway includes an output probe mounted on the output section of the waveguide isolator, the output probe having a coupling conductor extending into the waveguide isolator to couple the microwave EM energy therefrom, and
    wherein the first input includes an RF connector mounted on the waveguide isolator, the RF connector having a signal conductor that extends into the waveguide cavity to electrically contact the coupling conductor of the output probe.

2. Electrosurgical apparatus according to claim 1, wherein the waveguide isolator comprises a conductive input section, a conductive output section which mates with the input section to define a waveguide cavity within a volume enclosed by the input and output sections, and a DC isolation barrier arranged between the input and output sections,
    wherein the output on the common signal pathway includes a signal conductor and a ground conductor, and
    wherein the feed structure includes a capacitive structure between the ground conductor of the output on the common signal pathway and the conductive input section of the waveguide isolator, the capacitive structure being arranged to inhibit coupling of the RF EM energy and leakage of the microwave EM energy.

3. Electrosurgical apparatus according to claim 2, wherein the capacitive structure is provided by the DC isolation barrier and a microwave choke formed on the input section of the waveguide isolator.

4. Electrosurgical apparatus according to claim 3, wherein an inner section and an outer section of the waveguide isolator define a cylindrical body, and wherein the microwave choke comprises an annular channel extending axially from the distal end of the inner section of the waveguide isolator.

5. Electrosurgical apparatus according to claim 2, wherein the DC isolation barrier includes a rigid insulating spacer element mounted between an inner section and an outer section of the waveguide isolator.

6. Electrosurgical apparatus according to claim 5, wherein the DC isolation barrier includes an insulating film mounted on a portion of an inner surface of an input section at a junction with the rigid insulating spacer element.

7. Electrosurgical apparatus according to claim 6, wherein the insulating film extends away from the rigid insulating spacer element along the inner surface of the input section.

8. Electrosurgical apparatus according to claim 1, wherein the position at which the signal conductor of the RF connector makes electrical contact on the coupling conductor is adjustable.

9. Electrosurgical apparatus according to claim 1, wherein the first and second inputs to and the output from the combining circuit are electrically floating with respect to the RF signal generator and microwave signal generator.

10. Electrosurgical apparatus according to claim 1, including a voltage transformer having a primary coil connected to receive RF energy from the RF signal generator, and a secondary coil for delivering the RF signal to the RF channel, wherein the voltage transformer is arranged to output RF pulses having a peak voltage greater than or equal to 5 kV.

11. Electrosurgical apparatus according to claim 1, wherein the combining circuit is located in a housing, and the probe is connectable to an output port formed in the housing.

12. Electrosurgical apparatus according to claim 11, comprising an insulating sleeve at the output port of the housing to isolate the housing from the combining circuit.

13. Electrosurgical apparatus according to claim 1 including a controller operable to select an energy delivery profile for the RF EM radiation and the microwave EM radiation.

14. Electrosurgical apparatus according to claim 13 including an RF signal detector for sampling current and voltage on the RF channel and generating therefrom a RF detection signal indicative of the phase difference between the current and voltage, wherein the controller is in communication with the RF signal detector to receive the RF detection signal and is arranged to select the energy delivery profile for the RF EM radiation based on the RF detection signal.

15. Electrosurgical apparatus according to claim 13 including a microwave signal detector for sampling forward and reflected power on the microwave channel and generating therefrom a microwave detection signal indicative of the magnitude and/or phase of microwave power delivered by the probe, wherein the controller is in communication with the microwave signal detector to receive the microwave detection signal and is arranged to select the energy delivery profile for the microwave EM radiation based on the microwave detection signal.

16. Electrosurgical apparatus according to claim 1, wherein the distal end of the probe comprises a bipolar emitting structure comprising a first conductor spatially separated from a second conductor, the first and second conductors being arranged to act:
as active and return electrodes respectively to convey the RF EM radiation by conduction, and
as an antenna or impedance transformer to convey the microwave EM radiation by radiation.

17. Electrosurgical apparatus according to claim 1, wherein the first frequency is a stable fixed frequency in the range 10 kHz to 300 MHz and the second frequency is a stable fixed frequency in the range 300 MHz to 100 GHz, the second frequency being at least an order of magnitude higher than the first frequency.

18. An isolating circuit for electrosurgical apparatus for resection of biological tissue, the isolating circuit comprising:
a combining circuit having a first input connectable to receive radiofrequency (RF) electromagnetic (EM) radiation having a first frequency from an RF channel, a second input connectable to receive microwave EM radiation having a second frequency that is higher than the first frequency from a microwave channel, and an output in communication with the first and second inputs for conveying the RF EM radiation and the microwave EM radiation to a common signal pathway, and
a waveguide isolator connected to isolate the microwave channel from the RF EM radiation,
wherein the waveguide isolator comprises a conductive input section, a conductive output section which mates with the input section to define a waveguide cavity within a volume enclosed by the input and output sections, and a DC isolation barrier arranged between the input and output sections,
wherein the output from the combining circuit includes a signal conductor and a ground conductor,
wherein the output from the combining circuit includes an output probe mounted on the output section of the waveguide isolator, the output probe having a coupling conductor extending into the waveguide isolator to couple the microwave EM energy therefrom,
wherein the first input includes an RF connector mounted on the waveguide isolator, the RF connector having a signal conductor that extends into the waveguide cavity to electrically contact the coupling conductor of the output probe, and
wherein the isolating circuit comprises a capacitive structure between the ground conductor of the output from the combining circuit and the conductive input section of the waveguide isolator, the capacitive structure being arranged to inhibit coupling of the RF EM energy and leakage of the microwave EM energy.

19. The isolating circuit according to claim 18, wherein the capacitive structure is provided by the DC isolation barrier and a microwave choke formed on the input section of the waveguide isolator.

20. Electrosurgical apparatus according to claim 19, wherein an inner section and an outer section of the waveguide isolator define a cylindrical body, and wherein the microwave choke comprises an annular channel extending axially from a distal end of the inner section of the waveguide isolator.

21. Electrosurgical apparatus according to claim 18, wherein the DC isolation barrier includes a rigid insulating spacer element mounted between an inner section and an outer section of the waveguide isolator.

* * * * *